United States Patent
Cuzin et al.

(10) Patent No.: US 6,861,515 B2
(45) Date of Patent: Mar. 1, 2005

(54) ANALYSIS OF BIOLOGICAL TARGETS USING A BIOCHIP COMPRISING A FLUORESCENT MARKER

(75) Inventors: Marc Cuzin, Corenc (FR); Philippe Peltie, Saint-Paul-de-Varces (FR); Marc Fontecave, Saint-Ismier (FR); Jean-Luc Decout, Vaulnaveys le Haut (FR); Cécile Dueymes, Rodez (FR)

(73) Assignees: Commissariat a l'Energie Atomique, Paris (FR); Universite Joseph Fourier De Grenoble, Grenoble (FR)

( * ) Notice: Subject to any disclaimer, the term of this patent is extended or adjusted under 35 U.S.C. 154(b) by 57 days.

(21) Appl. No.: 10/203,780

(22) PCT Filed: Feb. 22, 2001

(86) PCT No.: PCT/FR01/00516

§ 371 (c)(1),
(2), (4) Date: Aug. 14, 2002

(87) PCT Pub. No.: WO01/63282

PCT Pub. Date: Aug. 30, 2001

(65) Prior Publication Data

US 2003/0165914 A1 Sep. 4, 2003

(30) Foreign Application Priority Data

Feb. 23, 2000 (FR) .......................................... 00 02236

(51) Int. Cl.⁷ ........................ C07H 21/00; C07H 21/02; C07H 21/04; C12Q 1/68
(52) U.S. Cl. .................... 536/23.1; 536/24.3; 536/25.2; 536/26.6; 435/6
(58) Field of Search ............................... 536/23.1, 24.3, 536/25.3, 26.6; 435/6

(56) References Cited

U.S. PATENT DOCUMENTS

| | | | |
|---|---|---|---|
| 5,578,832 A | 11/1996 | Trulson et al. |
| 5,646,411 A | 7/1997 | Kain et al. |
| 5,843,655 A | 12/1998 | McGall |
| 5,861,247 A | 1/1999 | Mirzabekov et al. |
| 5,876,930 A | 3/1999 | Flood et al. |
| 5,925,525 A | 7/1999 | Fodor et al. |

FOREIGN PATENT DOCUMENTS

| | | |
|---|---|---|
| WO | 99 05320 | 2/1999 |
| WO | 99 13105 | 3/1999 |
| WO | 99 60158 | 11/1999 |
| WO | 01 38585 | 5/2001 |

OTHER PUBLICATIONS

C. Frier et al.: "Method for preparing new flavin derivatives: Synthesis of flavin–thymine nucleotides and flavin–oligonucleotide adducts" Journal of Organic Chemistry, 62/11, pp. 3520–3528 1997.

J. Yguerabide et al.: "Pyrene–labeled DNA probes for homogenous detection of complementary DNA sequences: Poly (C) model system" Analytical Biochemistry, vol. 241, No. 2, pp. 238–247 Oct. 15, 1996.

Michel Bellis et al.: "La puce ADN: un multi–reacteur de paillasse" Medicine/Sciences, vol. 13, pp. 1317–1324 11/97.

*Primary Examiner*—Jezia Riley
(74) *Attorney, Agent, or Firm*—Oblon, Spivak, McClelland, Maier & Neustadt, P.C.

(57) ABSTRACT

This invention relates to an analytical support containing a plurality of oligonucleotides fixed on this support, where each of the nucleotides is marked by a fluorescent compound that presents a variation of fluorescence on the hybridization of each marked oligonucleotide with at complementary oligonucleotide. This support makes it possible to carry out an analysis of biological targets by measuring the variation of fluorescence in order to determine the hybridization of the targets with the oligonucleotides of the support.

17 Claims, 4 Drawing Sheets

SEQUENCE LISTING

<160> NUMBER OF SEQ ID NOS: 13

<210> SEQ ID NO 1
<211> LENGTH: 45
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
ctcatcgtgt aaaaaaaaaa aggcagtact ggaagggcta attct                45

<210> SEQ ID NO 2
<211> LENGTH: 45
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
ctcatcgtga attctaaaaa aaaaaaaaaa agctagcggc agtac                45

<210> SEQ ID NO 3
<211> LENGTH: 45
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
agaattagcc cttccagtac tgccttttt tttttacacg atgag                 45

<210> SEQ ID NO 4
<211> LENGTH: 45
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
gatctgccgc tagcttttt ttttttttt agaattcacg atgag                  45

<210> SEQ ID NO 5
<211> LENGTH: 15
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: modified_base
<222> LOCATION: (5)..(5)
<223> OTHER INFORMATION: c is methylated

<400> SEQUENCE: 5
ttttctttgg ggggt                                                 15

<210> SEQ ID NO 6
<211> LENGTH: 39
<212> TYPE: DNA
<213> ORGANISM: ARTIFICIAL SEQUENCE
<220> FEATURE:
<223> OTHER INFORMATION: SYNTHETIC DNA

-continued

```
<400> SEQUENCE: 6
cagtcccccc ttttcttttta aaaagtggct aagatctac                        39

<210> SEQ ID NO 7
<211> LENGTH: 39
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
gtagatctta gccacttttt aaaagaaaag gggggactg                         39

<210> SEQ ID NO 8
<211> LENGTH: 11
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: modified_base
<222> LOCATION: (1)..(1)
<223> OTHER INFORMATION: t is modified with a covalent linkage to flavin

<400> SEQUENCE: 8
tttttttttt t                                                      11

<210> SEQ ID NO 9
<211> LENGTH: 16
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: modified_base
<222> LOCATION: (1)..(1)
<223> OTHER INFORMATION: t is modified with a covalent linkage to flavin

<400> SEQUENCE: 9
tttttttttt tttttt                                                 16

<210> SEQ ID NO 10
<211> LENGTH: 16
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: modified_base
<222> LOCATION: (1)..(1)
<223> OTHER INFORMATION: t is modified with a covalent linkage to flavin
<220> FEATURE:
<221> NAME/KEY: modified_base
<222> LOCATION: (4)..(4)
<223> OTHER INFORMATION: t is methylated

<400> SEQUENCE: 10
ttttcttttg gggggt                                                 16
```

```
<210> SEQ ID NO 11
<211> LENGTH: 11
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: modified_base
<222> LOCATION: (1)..(1)
<223> OTHER INFORMATION: t is modified with a covalent linkage to deaza
      flavin

<400> SEQUENCE: 11
tttttttttt t                                                              11

<210> SEQ ID NO 12
<211> LENGTH: 20
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: modified_base
<222> LOCATION: (1)..(1)
<223> OTHER INFORMATION: c is modified with a covalent linkage to flavin

<400> SEQUENCE: 12
cccccaccac ttcccctctc                                                     20

<210> SEQ ID NO 13
<211> LENGTH: 40
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
ctagcctgat gagaggggaa gtggtggggg agacatagcc                                40
```

ANALYSIS OF BIOLOGICAL TARGETS USING A BIOCHIP COMPRISING A FLUORESCENT MARKER

TECHNICAL FIELD

This invention has for object an analytical support or "biochip" for the determination of DNA or RNA biological targets.

This analytical support finds application in numerous fields, in particular in biology for the sequencing of genomes, the research of mutations, the development of new medications, etc.

STATE OF PRIOR TECHNIQUE

An analytical support of this type comprises a plurality of oligonucleotide probes capable of giving rise to hybridization with the biological targets to be analyzed. The hybridization corresponds to the pairing of the target-strands with the complementary DNA strands on the support. In order to determine the nature of the targets, it is therefore necessary to be able to locate which sites of the support and therefore which nucleotides have given rise to a hybridization.

The document Médecine/Sciences, vol. 13, No. 11, 1997, pp. 1317–1324 [1] describes analytical supports of this type.

Usually the hybridization of biological targets on the support is determined by means of a fluorescent marker that is associated with the biological targets, after extraction of the zones of interest (lysis and possible amplification).

After putting the marked targets in contact with the analytical support comprising the oligoprobes, the sites where hybridization took place are determined by carrying out an excitation of the set of fluorescent markers, followed by a reading of the sites in order to detect the fluorescence light re-emitted by the markers. The sites for which fluorescence light is detected are those that have fixed the target molecules. The reading systems adapted to various biochips are described, for example, in U.S. Pat. No. 5,578,832 [2] and U.S. Pat. No. 5,646,411 [3].

This technique presents the disadvantage of necessitating the marking of the biological target before putting it in contact with the analytical support, which poses certain practical problems concerning the quantification and/or efficiency of the marking and the time allowed to carry it out. Moreover, marking at a given step fixes the situation and prevents carrying out later on dynamic measures capable of following a hybridization reaction.

It may also be noted that the manufacture of analytical supports or "biochips" is carried out by various methods that all pose the problem of the final control of the quality of the supports that are obtained.

As a matter of fact, the quantity of probes deposited on the support, the sites of the support or contacts, or in the cavities provided for in this support, poses the problem of the effective control of the presence of the oligoprobes. No method exists at present to quantify and localize with precision the oligoprobes deposited or constructed in situ on an analytical support made, for example, of silicon, glass or plastic, for example nylon.

Exposition of the Invention

This invention has precisely for object an analytical support, or biochip, that makes it possible to ensure under the best conditions the preliminary control of manufacture, and to then facilitate and make more sensitive the determination of the sites of the support on which hybridization has occurred.

According to the invention, the analytical support comprises a plurality of oligonucleotides fixed on this support, and it is characterized in that each of the said oligonucleotides is marked by a fluorescent compound such that the fluorescence of an oligonucleotide marked by this compound is attenuated after hybridization of this marked oligonucleotide with a complementary oligonucleotide.

The attenuation of fluorescence may consist in a variation in the intensity of fluorescence, a variation in the time constant of the fluorescence, or a spectral shifting in wavelength of the fluorescence.

With such an analytical support, it is no longer necessary to mark the targets that are to be analyzed, because the localization of the hybridization sites may be detected by checking the variation of fluorescence obtained at the time of hybridization on the oligonucleotide sites concerned.

According to the invention, a fluorescent compound presenting an intensity of fluorescence attenuated by hybridization is more preferably used. More preferably, this attenuation represents 30 to 99% of the intensity of fluorescence before hybridization.

Fluorescent compounds presenting these characteristics may be made from, for example, flavin, deazaflavin and their derivatives. Such compounds may be fixed on oligonucleotides through a spacing arm, for example of the type —(CH$_2$)$_n$—, to give flavin (deazaflavin)-oligonucleotide conjugates. A synthesis of conjugates of this type is described by C. Frier et al in J. Org. Chem., 62, 1997, pages 3520–3528 [4].

This synthesis consists in fixing a derivative of flavin on the oligonucleotide by a phosphoramidite or H-phosphonate coupling method starting from a derivative of the formula:

(I)

with n being an integer from 2 to 8, for example 6.

The synthesis strategy makes it possible to introduce the flavinic group, including with automated oligonucleotidic synthesis methods. This synthesis can also be used for the manufacture of oligonucleotide-deazaflavin conjugates.

Thus the oligonucleotide is marked by a group of the formula —(CH$_2$)$_n$—R$^1$ in which n is an integer from 2 to 8, and R$^1$ represents a group corresponding to one of the following formulas:

The use of flavin, deazaflavin or their derivatives as fluorescent compound in the invention is particularly interesting.

As a matter of fact, flavins are molecules endowed with an intense yellow-green fluorescence, very characteristic. The fluorescence excitation spectrum is identical to the absorption spectrum of visible light, with 2 maxima at 374 and 446 nanometers, and their fluorescence emission spectrum consists in a broad band with a maximum around 520 nanometers. The deazaflavins absorb around 320 and 396 nanometers and present fluorescence intensities (emission at 452 nanometers) more significant than the flavins.

According to the invention, it was discovered that the coupling of the flavin to an oligonucleotide did not significantly modify these fluorescence properties in aqueous medium, the maxima of excitation and of emission as well as the intensities being the same for the free flavin and for the oligonucleotide-flavin conjugate.

In another connection, up to a concentration of 100 µmol/L of conjugate, there is an excellent linearity between the intensity of fluorescence and the concentration.

It is however necessary to note an effect of salt on the intensity of fluorescence, namely the fact that increasing concentrations of NaCl have an increasing effect of extinction "quenching" of the fluorescence of the flavins. It is the same with the conjugates. This must be noted because the hybridization necessitates NaCl concentrations from 0.1 to 1 M to promote the formation of the duplex (association of an oligonucleotide with its complementary oligonucleotide).

According to the invention, it was discovered that when an oligonucleotide-flavin conjugate is incubated with an equivalent of its complementary target oligonucleotide, there is a disappearance of 90 to 100% of the specific fluorescence of the flavin.

This effect was profited from in the invention to facilitate the reading of the sites of hybridization on the biochips.

Consequently the invention also has for object a method for analysis of biological targets by putting these targets in contact with an analytical support comprising a plurality of oligonucleotides, and determination of a (some) hybridization(s) between the targets and the oligonucleotides of the support, characterized in that each of the oligonucleotides of the support is marked by a fluorescent compound that presents a variation of fluorescence on hybridization of the marked oligonucleotide with the complementary oligonucleotide, and in that the oligonucleotides of the support which have given rise to a hybridization are determined by measurement of the fluorescence corresponding to each oligonucleotide of the support before and after putting the support in contact with the targets.

In this method, the analytical support of the invention that presents the characteristics described previously is therefore used.

According to a variant of this method, the targets also are marked by a second fluorescent compound whose emission wavelength is different from that of the fluorescent compound of the oligonucleotides, or first fluorescent compound, and the oligonucleotides that have given rise to a variation of fluorescence are controlled by measurement of this second compound.

In this case, the fluorescent compound of the oligonucleotides of the support, or first fluorescent compound, is chosen from among flavin, deazaflavin and their derivatives, and the second fluorescent compound is chosen from among stable fluorophores used on DNA chips and preferentially emitting in the visible (Rhodamine, $CY_3$, $CY_5$, etc.), for example shifted towards the red with respect to flavin.

With the analytical support of the invention whose oligonucleotides are marked by a fluorescent compound, a control of the quality of the support can also be performed.

Consequently the invention also has for object a method of control of an analytical support comprising a plurality of oligonucleotides fixed on that support, characterized in that the fixed oligonucleotides are oligonucleotides marked by a fluorescent compound and in that the quantity of oligonucleotides fixed on the support is localized and determined by measurement of the fluorescence of the fluorescent compound.

Other characteristics and advantages of the invention will appear more clearly upon reading of the description which follows, given of course as illustration and not exhaustively, with reference to the appended drawings.

DETAILED EXPOSITION OF THE EMBODIMENTS

In the examples that follow, the following oligonucleotides are used:

```
Target T11
5'ctcatcgtgt aaaaaaaaaa aggcagtact ggaagggcta attct3' (SEQ ID NO: 1)

Target T16
5'ctcatcgtga attctaaaaa aaaaaaaaaa agctagcggc agtac3' (SEQ ID NO: 2)

Complementary oligonucleotide of SEQ ID NO: 1
3'gagtagcaca tttttttttt tccgtcatga ccttcccgat taaga5' (SEQ ID NO: 3)

Complementary oligonucleotide of SEQ ID NO: 2
3'gagtagcact taagattttt tttttttttt tcgatcgccg tcatg5' (SEQ ID NO: 4)

HIV oligonucleotide
5'-ttttcmettttg gggggt-3'                            (SEQ ID NO: 5)

Double strand of HIV target (SEQ ID NO: 6 and 7)
5'cagtccccccc ttttcttttta aaaagtggct aagatctac3'     (SEQ ID NO: 6)

3'gtcaggggggg aaaagaaaat ttttcaccga ttctagatg5'       (SEQ ID NO: 7)
```

EXAMPLE 1

In this example, flavin-oligonucleotide $T_{11}$ and flavin-oligonucleotide $T_{16}$ conjugates are prepared by following the procedure described in document [4] using the derivative of flavin F1 of formula (I) with n=6. Thus is obtained the conjugate (SEQ ID NO: 8) of formula:

In the same way a flavin-$T_{16}$ conjugate (SEQ ID NO: 9) is prepared of formula:

Finally, the HIV-flavin conjugate is prepared using the flavin derivative of formula (I) with n=6. (SEQ ID NO: 10) of formula:

In the same way the $T_{11}$-deazaflavin DF1 conjugate (SEQ ID NO: 11) is prepared of formula:

EXAMPLE 2

In this example, the influence of the presence of another oligonucleotide on the fluorescence emission of the $T_{11}$-flavin conjugate (SEQ ID NO: 8) is studied.

To this purpose, 0.1 to 10 μmol/L of the $T_{11}$-flavin conjugate is put in the presence of 1 equivalent of the oligonucleotide (SEQ ID NO: 1) in a 10 mM Tris-HCl buffer, pH 7.0 with 0.1 mM–1M NaCl.

Excitation is effected at 460 nanometers and fluorescence emission is measured in the neighborhood of 540 nanometers.

Under these conditions, fluorescence emission does not represent more than 5% of the emission measured with the $T_{11}$-flavin conjugate alone.

This operation is begun again in the presence of the oligonucleotide (SEQ ID NO: 3), namely the complementary oligonucleotide of SEQ ID NO: 1. Under these conditions, fluorescence emission represents 98% of the fluorescence emission of the $T_{11}$-flavin conjugate. The presence of this oligonucleotide therefore had no influence on the fluorescence emission of the $T_{11}$-flavin conjugate.

If this operation is begun again by adding 1 equivalent of the oligonucleotide SEQ ID NO: 1 and 1 equivalent of the oligonucleotide SEQ ID NO: 3, under conditions in which the duplex cannot form, fluorescence emission represents 6% of the fluorescence emission of the conjugate alone.

Thus, it is clear that the presence of the complementary target (SEQ ID NO: 1) of the $T_{11}$ oligonucleotide leads to a disappearance of 90 to 100% of the specific fluorescence of the flavin.

EXAMPLE 3

The same experiments are carried out on the $T_{16}$-flavin conjugate (SEQ ID NO: 9), either in the presence of the $T_{16}$ target (SEQ ID NO: 2), or in the presence of the oligonucleotide (SEQ ID NO: 4), complementary to (SEQ ID NO: 2), or in the presence of a mixture of the two oligonucleotides SEQ ID NO: 2 and SEQ ID NO: 4, under conditions in which the duplex cannot form.

The following results are obtained:

| Oligonucleotides | Emission at 540 nm |
|---|---|
| $T_{16}$-flavin (SEQ ID NO: 9), | 100% |
| With its target (SEQ ID NO: 2), | 2% |
| With the oligonucleotide (SEQ ID NO:4) Complementary to the target, | 91% |

-continued

| Oligonucleotides | Emission at 540 nm |
|---|---|
| With SEQ ID NO: 2 and SEQ ID NO: 4, (conditions in which duplex cannot form) | 4% |

Thus, as in the case of example 2, the presence of the target (SEQ ID NO: 2) of the $T_{16}$ oligonucleotide leads to an extinction of fluorescence of the flavin because of the hybridization between the target and the $T_{16}$ oligonucleotide.

EXAMPLE 4

In this example, the properties of the HIV nucleotide conjugated with flavin (SEQ ID NO: 10) are tested, in the presence of the HIV duplex formed by SEQ ID NO: 6 and SEQ ID NO: 7.

Under these conditions, fluorescence emission represents 90% of the initial emission. There was no hybridization between the F1-HIV conjugate and the duplex since the HIV target had already given rise to a hybridization.

Examples 2 to 4 thus show that the extinction of fluorescence is specific for the formation of a duplex between the oligonucleotide-flavin conjugate and the complementary oligonucleotide for the following reasons:

1) An elevation of temperature, which leads to a destabilization of the duplex and to a displacement of the equilibrium: double-strand→single strands causes the intensity of fluorescence to go back up. It is to be noted that fluorescence spectroscopy therefore constitutes a good method for evaluating the association constants at a given temperature. A new drop in temperature again decreases the fluorescence intensity.

2) The addition of an oligonucleotide not complementary to the conjugate does not lead to a decrease in the fluorescence.

3) The addition of a double strand, complementary to the conjugate, to a solution of the oligonucleotide-flavin conjugate under conditions that lead to triplex formation do not lead to an extinction of fluorescence, as appears in example 4.

4) When the target is a complementary RNA, a decrease of fluorescence is also observed, but to a lesser degree.

It can further be noted that the doublet gg adjacent to the $A_{11}$ sequence of the oligonucleotide SEQ ID NO: 1, which does not participate in the pairing, is not necessary since identical results were obtained with oligonucleotides identical to SEQ ID NO: 1, but comprising the sequences gc, cg and cc in place of gg.

EXAMPLE 5

This example studies the influence of the presence of the target oligonucleotide SEQ ID NO: 1 at concentrations ranging up to 1.5 equivalent for 1 equivalent of the $T_{11}$-deazaflavin conjugate (SEQ ID NO: 11) on the fluorescence of the deazaflavin of the conjugate. The same conditions were used as those of examples 2, 3 and 4.

Figure 1:
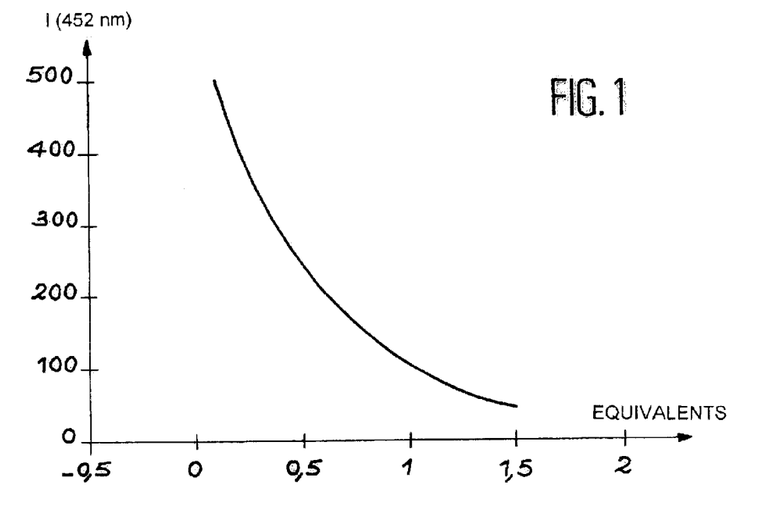
FIG. 1 is a curve showing the evolution of the fluorescence intensity of the conjugate $T_{11}$-deazaflavin as a function of the number of equivalents of the target poly A (SEQ ID NO: 1).

FIG. 1 shows the results obtained, namely the evolution of fluorescence intensity at 452 nanometers as a function of the number of equivalents of the poly A target (SEQ ID NO: 1).

EXAMPLE 6

In this example, the same experiment as in example 5 is carried out, but by using as conjugate the $T_{11}$-flavin conjugate (SEQ ID NO: 8).

Figure 2:
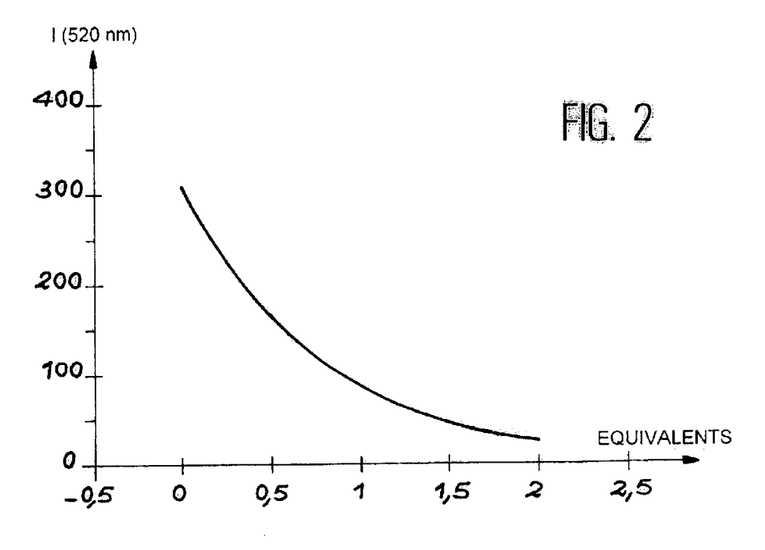
FIG. 2 is a curve showing the evolution of the fluorescence intensity of the conjugate $T_{11}$-flavin as a function of the number of equivalents of poly A targets (SEQ ID NO: 1).

FIG. 2 shows the results obtained, namely the fluorescence intensity at 520 nanometers as a function of the number of equivalents of the poly A target (SEQ ID NO: 1).

A comparison of FIGS. 1 and 2 shows that the deviations of fluorescence are more significant with the deazaflavin which is on that account more sensitive.

EXAMPLE 7

In this example, the stability of the complex of $T_{11}$-flavin (SEQ ID NO: 8) with the complementary SEQ ID NO: 1 is studied. Experiments of gel-retardation and measurement of fusion temperature $T_m$ are carried out. It was thus possible to show that the presence of a flavin or of a deazaflavin at the end of an oligonucleotide confers a significant increase in stability to the complex that this oligonucleotide makes with the complementary oligonucleotide.

For example, at an NaCl concentration of 0.1 M, the $T_{11}$ sequence leads to a complex with the oligonucleotide SEQ ID NO: 1 with a $T_m$ of 23° C. (37° C. at 1 M NaCl), while the $T_{11}$-flavin conjugate (SEQ ID NO: 8) gives with SEQ ID NO: 1 a complex with a $T_m$ of 28° C. (42° C. at 0.1 M NaCl).

Gel-retardation experiments show that the formation of the duplex necessitates much smaller quantities of the $T_{11}$-flavin conjugate (SEQ ID NO: 8) than of the $T_{11}$ oligonucleotide without flavin.

Similar results were found with the $T_{16}$-flavin conjugate (SEQ ID NO: 9) and the target (SEQ ID NO: 2) with respect to $T_{16}$ without flavin.

The study of the conjugates of oligonucleotide-flavins (SEQ ID NO: 8 and 9) reveals an altogether interesting property of these molecules:

- the presence of the flavin stabilizes the association of this conjugate with the complementary oligonucleotide by a mechanism still poorly understood (hydrogen bonds between the flavin and the nucleotide bases, stacking, . . . )
- this association leads to a very significant decrease in fluorescence (extinction in certain cases),
- this extinction of fluorescence is very specific: it occurs only when the conjugate is in the presence of the complementary oligonucleotide, under conditions of formation of the duplex.

EXAMPLE 8

In this example, a conjugate formed from an oligonucleotide of 20 bases and from flavin (SEQ ID NO: 12):

was put in contact with the complementary oligonucleotide (SEQ ID NO: 13):

ctagcctgat gagaggggaa gtggtggggg agacatagcc at increasing concentration, under the same conditions as those of examples 2 to 4, and the fluorescence spectrum in the neighborhood of 520 nanometers was measured with the spectrofluorometer.

The wavelength of excitation is 446 nanometers and the maximum emission corresponding to the flavin is at 520 nanometers.

The measurement is carried out instantaneously, then 5 minutes after, with each time a higher concentration of the complementary target (SEQ ID NO: 13).

Figure 3:
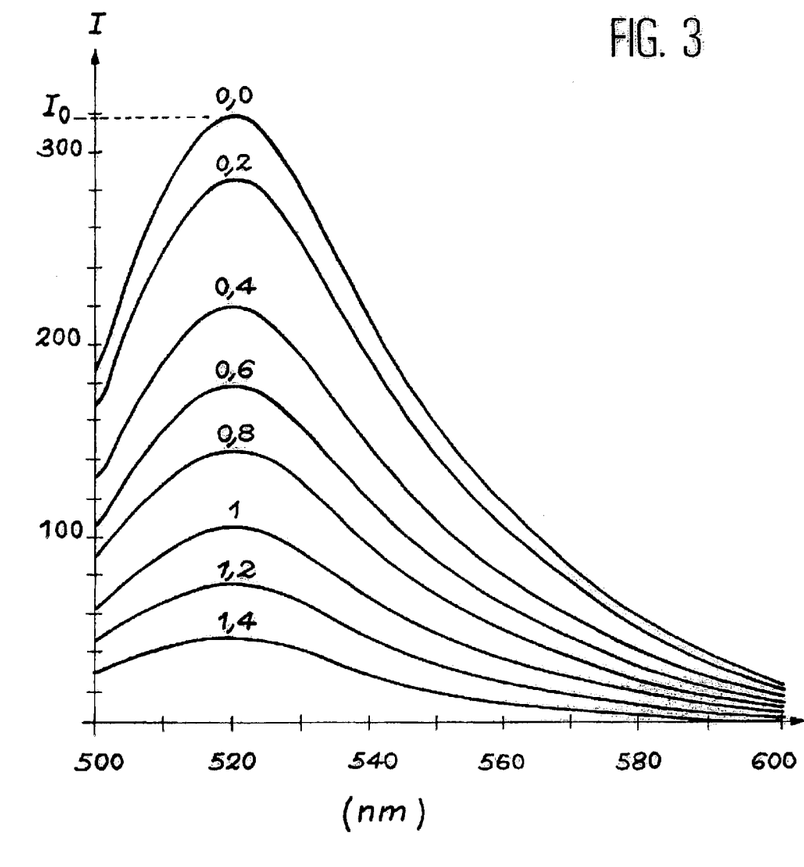
FIG. 3 shows the fluorescence spectra obtained by hybridization of the conjugate SEQ ID NO: 12-flavin with the complementary oligonucleotide (SEQ ID NO: 13) for increasing additions of equivalents of the complementary sequence.

FIG. 3 shows the fluorescence spectra obtained without complementary oligonucleotide, and then with 0.2, 0.4, 0.6, 0.8, 1, 1.2 and 1.4 equivalents of the complementary oligonucleotide SEQ ID NO: 13.

Starting from an initial intensity of 318 in the absence of the target (the complementary oligonucleotide), an extinction of fluorescence of a ratio of approximately 20 is observed when the complementary target is put in slight excess.

The extinction may correspond to various processes which may be either a transfer of energy, an extinction by collision ("collisional quenching"), or complex formation ("static quenching") which corresponds to probe-target hybridization.

Extinction by collision or "collisional quenching" occurs when there is a collision between the fluorescent compound (flavin) and the extincting oligonucleotide at concentration [Q]. It is described by the Law of Stern-Volmer which corresponds to the following equation:

$$I_0/I = 1 + h_q \tau_0 [Q]$$

where $h_q$ represents the extinction constant and $\tau_0$ is the fluorescence lifetime.

The Stern-Volmer constant is defined in the following way:

$$K_D = h_q \tau_0.$$

In this case, on the one hand, the lifetime becomes $\tau$ and $I_0/I = \tau_0/\tau$, and on the other hand the temperature has the effect of augmenting the phenomenon, $K_D$ increasing when the temperature increases.

Figure 4:
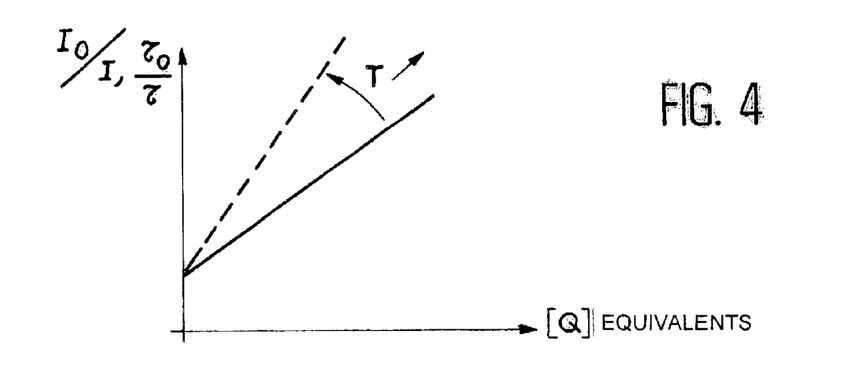
FIG. 4 shows the evolution of the ratio of fluorescence intensities $I_0/I$ as a function of the concentration [Q] of fluorescent compound in the case of a dynamic extinction.

FIG. 4 shows the evolution of $I_0/I$ and of $\tau_0/\tau$ as a function of [Q]. When the temperature is increased, the slope from the right increases.

In the case of an extinction by complex formation, that is to say in the case which interests us, the probe/target hybridization, namely "static quenching", the Law of Stern-Volmer becomes:

$$I_0/I = 1 + K_s[Q]$$

where $K_s$ is the association constant.

Figure 5:
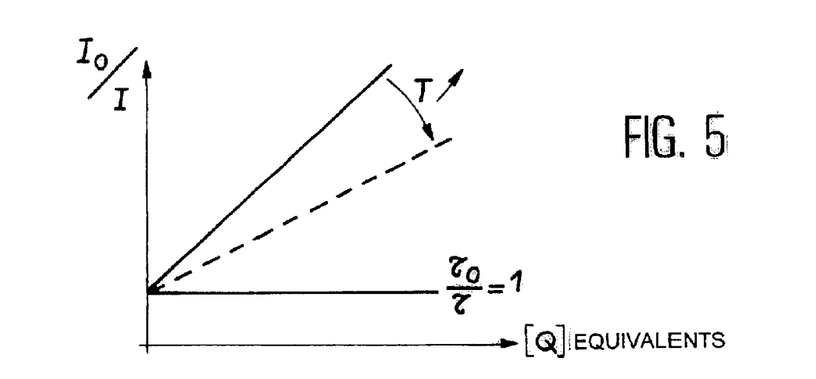
FIG. 5 shows the evolution of the ratio of fluorescence intensities $I_0/I$ as a function of the concentration [Q] of fluorescent compound in the case of a static extinction.

FIG. 5 shows the evolution of $I_0/I$ as a function of [Q]. In this case, $\tau_0/\tau = 1$ and the slope decreases when the temperature increases, which is normal since an increase in temperature causes a partial denaturation of the complex, therefore the fluorophore which was extinguished is liberated.

Figure 6:
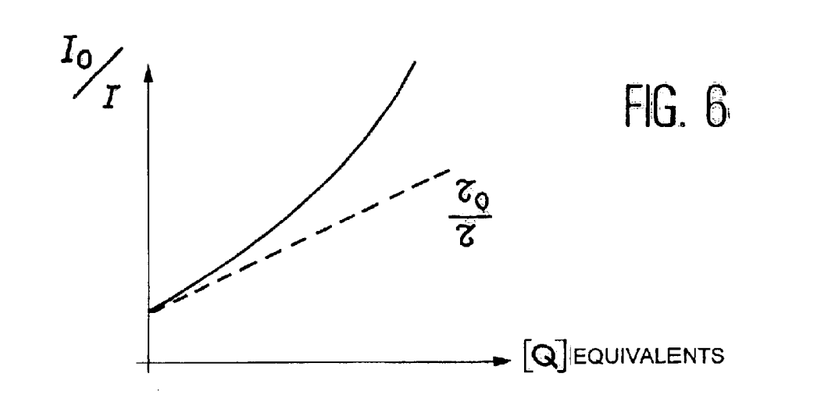
FIG. 6 shows the evolution of the ratio $I_0/I$ as a function of the concentration [Q] of fluorescent compound in the case of a combined action of static and dynamic extinction.

In most cases, as shown in FIG. 6, a combined action of static and dynamic quenching is found conjointly, which is expressed by a positive curvature towards the y axis. The relation of Stern-Volmer must thus be modified:

$$I_0/I = 1 + (K_d + K_s)[Q] + K_d K_s [Q]^2$$

Figure 7:
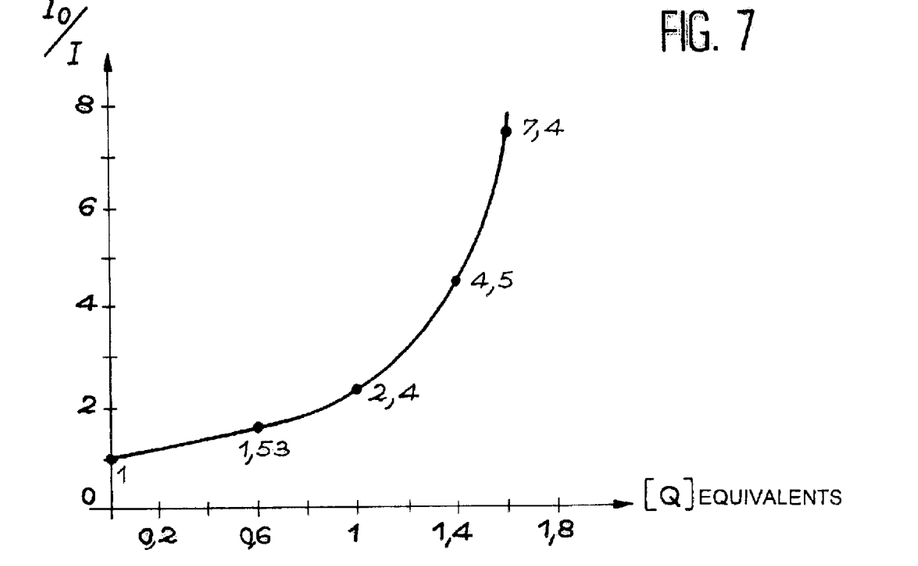
FIG. 7 is a curve showing the evolution $I_0/I$ as a function of the concentration [Q] of flavin in the case of the spectra shown in FIG. 3.

If one returns to the fluorescence spectra shown in FIG. 3, and if one traces the law $I_0/I$ as a function of [Q] from the spectra, one finds in fact a positive curvature and not a straight line, which expresses the simultaneous presence of static and dynamic quenching, as appears in FIG. 7.

Figure 8:
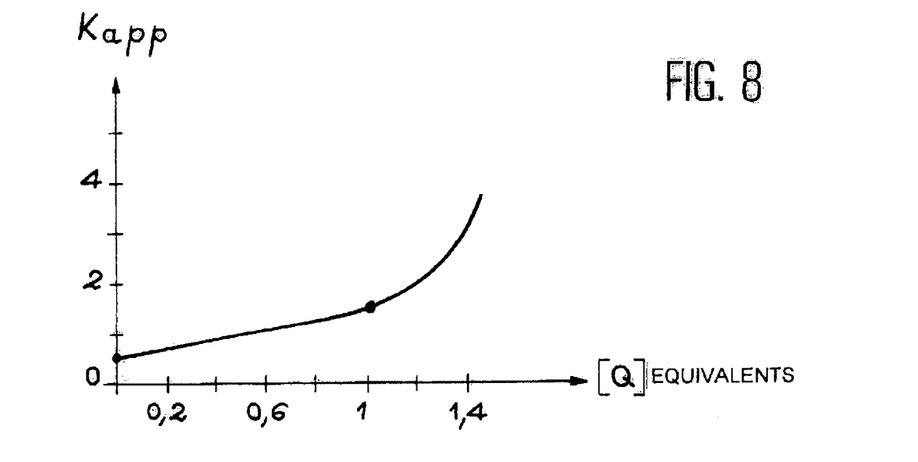
FIG. 8 is a curve showing the evolution of the apparent constant Kapp as a function of the concentration [Q] of flavin in the case of the spectra of FIG. 3.

FIG. 8 shows the variation of $K_{app}$ as a function of the concentration [Q] in equivalents from the results of FIG. 3.

A second fluorophore, not subject to quenching and strongly shifted in fluorescence wavelength with respect to the fluorescent compound, is coupled to the target. Thus, this fluorophore can be excited concurrently and will reveal the effective presence of the hybridization complex.

In particular, a fluorochrome such as $CY_3$ can be used, which has an excitation wavelength equal to 543.5 nanometers and an emission wavelength equal to 580 nanometers. It may be visualized with a scanner using a low-power (1 mW) green HeNe laser as is done in a biochip reading system.

This double marking, namely that of the oligonucleotide fixed on the biochip by means of a first fluorescent compound such as flavin, and that of the targets to be determined by a second fluorescent compound such as $CY_3$, possesses undeniable advantages with respect to a simple conventional marking.

As a matter of fact, on immobilization of the probes on the biochip, the presence of the flavin allows a control of the quality of the probes before hybridization, by making a total image of the chip so that all sites possessing probes fluoresce. It is then possible to map the flaws of the chip (image that is non-homogeneous in fluorescence intensity); it is also possible to profit from redundance by putting the same type of probe on several contiguous sites.

At the hybridization phase, a decrease of fluorescence is observed on the sites concerned with a reading at 520 nanometers while exciting in the neighborhood of 400–450 nanometers. A reading of $CY_3$ then makes it possible to resolve the non-specificity since only the hybridized complexes will possess the $CY_3$ target conjointly with the decrease of fluorescence.

The significance of very distinct ranges of wavelengths resides in the fact that excitation at 400–450 nanometers to all intents and purposes does not make $CY_3$ fluoresce because this is very far from its absorption band (maximum absorption at 550 nanometers).

An interesting parameter that may be evaluated is the lifetime that, as has been seen, does not vary at the time of the formation of complexes but varies strongly in the case of dynamic quenching. The two phenomena in competition can therefore easily be separated: collisional quenching and the formation of hybrids which alone is interesting.

Another parameter that is appropriate to follow is the evolution of the fluorescence as a function of the temperature. As a matter of fact, in a conventional "chip", the fluorescence is read at a given temperature. Raising the temperature has the effect of "breaking" non-specific hybridizations (denaturation) but also has the troublesome effect of reducing the fluorescence of the complex (since the quantal yield of fluorescence decreases when the temperature increases). In the case of static quenching, it has been seen that temperature elevation, on the contrary, restores the fluorescence of the poorly-hybridized complexes since there is a "liberation" of the incriminated fluorophore.

Thus, the judicious association of a reading with 2 markers (flavin+conventional fluorophore), temperature control, and even measurement of lifetime, makes it possible to follow perfectly the formation of the hybrids and even to calculate the various constants (Stern-Volmer constant, association constant, and even calculation of the radii of the spheres of action).

References Cited

[1] Médecine/Sciences, vol. 13, No. 11, 1997, pp. 1317–1324

[2] U.S. Pat. No. 5,578,832

[3] U.S. Pat. No. 5,646,411

[4] C. Frier et al, J. Org. Chem., 62, 1997, pages 3520–3528.

What is claimed is:

1. Analytical support comprising a plurality of oligonucleotides fixed on this support, wherein each of said oligonucleotides is marked by a fluorescent compound such that the fluorescence of an oligonucleotide marked by this compound is attenuated after hybridization of this marked oligonucleotide with a complementary oligonucleotide, wherein said fluorescent compound is selected from the group consisting of flavin and deazaflavin.

2. Support according to claim 1, wherein the attenuation of fluorescence is a variation of fluorescence intensity, a variation of the time constant of the fluorescence, or a shift in wavelength of the fluorescence.

3. Analytical support according to claim 2, wherein the fluorescent compound presents a fluorescence intensity before hybridization.

4. Support according to claim 3, wherein the attenuation represents 30 to 99% of the fluorescence intensity before hybridization.

5. Support according to claim 1, wherein the fluorescent compound is flavin.

6. Support according to claim 1, wherein the fluorescent compound is deazaflavin.

7. Support according to claim 1, wherein the oligonucleotide is marked by a group of formula —$(CH_2)_n$—$R^1$ in which n is an integer from 2 to 8 and $R^1$ represents a group corresponding to one of the following formulas:

(II)

(III)

8. Support according to claim 4, wherein the oligonucleotide is marked by a group of formula —$(CH_2)_n$-$R^1$ in which n is an integer from 2 to 8 and $R^1$ represents a group corresponding to one of the formulas II and III 9. Support according to claim 7, wherein n is 6.

10. Support according to claim 8, wherein n is 6.

11. Control method for an analytical support comprising a plurality of oligonucleotides fixed on that support, wherein the fixed oligonucleotides are oligonucleotides marked by a fluorescent compound and further wherein the quantity of oligonucleotides fixed on the support is localized and determined by measurement of the fluorescence of the fluorescent compound, wherein the fluorescent compound is chosen from the group consisting of flavin and deazaflavin.

12. Method for analysis of biological targets by putting these targets in contact with an analytical support comprising a plurality of oligonucleotides and determination of a hybridization between targets and the oligonucleotides of the support, wherein an analytical support as claimed in claim 1 is used, and further wherein the oligonucleotides of the support which have given rise to a hybridization are determined by measurement of the fluorescence corresponding to each oligonucleotide of the support before and after putting the support in contact with the targets.

13. Method according to claim 12, wherein the targets are also marked by a second fluorescent compound whose emission wavelength is different from that of the fluorescent compound of the oligonucleotides, or first fluorescent compound, and the oligonucleotides that have given rise to a variation of fluorescence are controlled by measurement of the fluorescence of this second compound.

14. Method according to claim 12, wherein the fluorescent compound of the oligonucleotides of the support, or first fluorescent compound, is chosen from the group consisting of flavin and deazaflavin, and the second fluorescent compound is chosen from the group consisting of stable fluorophores shifted towards the red with respect to flavin.

15. Method as claimed in claim 12 wherein the fluorescence intensity of the first compound is measured by spectrometry.

16. Method according to claim 13, wherein the second fluorescent compound is $CY_3$ whose excitation wavelength is 543.5 nanometers and whose emission wavelength is 580 nanometers.

17. Method according to claim 16, wherein the presence of this second compound is determined with a scanner using a HeNe laser.

* * * * *